(12) United States Patent
Rheinberger et al.

(10) Patent No.: US 8,436,070 B2
(45) Date of Patent: May 7, 2013

(54) PASTY POLYMERIZABLE DENTAL COMPOUNDS AND METHOD FOR PRODUCING THE SAME

(75) Inventors: Volker Rheinberger, Vaduz (LI); Axel Kammann, Feldkirch (AT)

(73) Assignee: Ivoclar Vivadent AG, Schaan (LI)

( * ) Notice: Subject to any disclaimer, the term of this patent is extended or adjusted under 35 U.S.C. 154(b) by 590 days.

(21) Appl. No.: 12/310,185

(22) PCT Filed: Jun. 30, 2009

(86) PCT No.: PCT/EP2009/058230
§ 371 (c)(1),
(2), (4) Date: Jul. 6, 2010

(87) PCT Pub. No.: WO2010/000763
PCT Pub. Date: Jan. 7, 2010

(65) Prior Publication Data
US 2010/0286293 A1    Nov. 11, 2010

(30) Foreign Application Priority Data

Aug. 16, 2006  (DE) .......................... 10 2006 038 280
Jul. 30, 2007  (DE) .......................... 10 2007 035 735

(51) Int. Cl.
*C08F 2/46*    (2006.01)
*C08L 81/06*   (2006.01)

(52) U.S. Cl.
USPC ............ 523/113; 523/115; 433/167; 433/172

(58) Field of Classification Search .................. 523/113, 523/115; 433/167, 171
See application file for complete search history.

(56) References Cited

U.S. PATENT DOCUMENTS

| 2,793,436 | A | | 5/1957 | Gotlib |
| 4,156,766 | A | * | 5/1979 | Feldt .............................. 526/313 |
| 4,279,719 | A | * | 7/1981 | Hitzler et al. ................... 522/62 |
| 5,502,087 | A | | 3/1996 | Tateosian et al. |
| 6,605,651 | B1 | | 8/2003 | Stangel et al. |
| 7,122,134 | B2 | * | 10/2006 | Sasaki ........................... 252/582 |

FOREIGN PATENT DOCUMENTS

| EP | 0 059 525 | | 9/1982 |
| EP | 0 212 193 | | 3/1987 |
| EP | 0 584 376 | | 3/1994 |
| EP | 0 630 641 | | 12/1994 |
| EP | 0 687 451 | | 12/1995 |
| EP | 0 760 249 | | 11/1999 |
| FR | 2 648 345 | | 12/1990 |
| JP | 58072509 | | 4/1983 |
| JP | 61050906 | | 3/1986 |
| JP | 62124501 A | * | 6/1987 |
| WO | 2004/113042 | | 12/2004 |

OTHER PUBLICATIONS

J.P. Fouassier and J.F. Rabek (editors), Radiation Curing in Polymer Science and Technology, vol. II, Elsevier Applied Science, London and New York, 1993.

* cited by examiner

*Primary Examiner* — Irina S Zemel
(74) *Attorney, Agent, or Firm* — Ann M. Knab; Thad McMurray

(57) ABSTRACT

The present invention relates to a material for dental products comprising a mixture of at least one polymerizable monomer and at least one polymer based on polysulfones which is preswollen in a portion of the polymerizable monomer.

16 Claims, No Drawings

PASTY POLYMERIZABLE DENTAL COMPOUNDS AND METHOD FOR PRODUCING THE SAME

The present invention relates to single paste and multipaste systems for dental products, to a process for the preparation thereof and to the use thereof.

The commonest and most widespread preparation of prostheses is limited to the use of polymer/monomer systems (powder/liquid systems) which are stored in separate containers. Before use, both components, the polymer and the monomer, are mixed in a specific mixing ratio. After mixing, a dough-like kneadable material, caused by the solubility of the polymer in the monomer, is formed with a highly restricted stability on storage, which material is filled, poured or injected into a flask using well known filling; pouring or injection techniques and subsequently cured in this.

This simple mixing process for MMA/PMMA systems has proved itself over decades. The reasons for this widespread acceptance are not only the economic advantages but also the clinical stability and the mechanical properties exhibited by moldable and curable polymer/monomer systems based on this.

However, monomer/polymer mixtures according to the powder/liquid system have disadvantages, both as mixture and cured. With the powder/liquid system, polymer mixture and monomer mixture are stirred together individually, i.e. the dental technician, through his personal mixing technique, influences the property and quality of the mixture and accordingly of the completed polymerized prosthesis. The system actually comprises two mixing operations: first, the powder component (polymer) is stirred into the monomer and secondly, after maturing, the mixture is thoroughly kneaded individually by hand. After the powder component has been stirred into the liquid, sedimentation processes and nonhomogeneities may occur. After the powder component has been stirred in, swelling and dissolution processes begin simultaneously at the interfaces of the polymer particles, resulting in an increase in viscosity of the combined mixture. A portion of the polymer constituents dissolve in the monomer phase and change this, first via a syrup- or honey-like consistency, into a malleable dough.

If the dental technician terminates this maturing too soon, a "thin mixture" is formed in which the particles are insufficiently bonded by the liquid. On extruding the thinly impasted substance, the particles become separated from the liquid phase in the flask, resulting in color problems and unsatisfactory mechanical properties. This dough-like paste or material has to be formed in a closed receptacle, otherwise the dried-out particles of the dough, in particular with self-polymerizing systems, frequently cause air pockets, crumbly edge sections and a substandard dental composite.

If the swelling process in the closed receptacle is left for too long, the dough becomes excessively mature. The malleability decreases, prevents the functionally appropriate extrusion of the material and results in the formation of grooves and likewise in an unsatisfactory dental composite.

Once the dough-like material is pressed into the flask, the continuously progressing swelling and dissolution process of the polymer/monomer mixture in the flask is accelerated by warming. Shortly before the beginning of the radical polymerization, a horny material which is as tough as leather is produced which no longer loses its shape through the warming and the thermal expansion an increase in the pressure in the flask brought about by this.

During the polymerization, the formerly highly viscous polymer solution changes into a stable and solid polymer matrix which now firmly encloses the particles of the polymer or holds them in the structure. These polymer particles frequently contain defects, such as air bubbles and crosslinked constituents. These defects become exposed on milling and grinding the surfaces of the prostheses. Microscopically small pores are formed in which, when the prosthesis is in place, a biofilm is preferably formed on which bacteria are deposited in future.

In view of the difficulties described in the handling of powder/liquid systems, single-component and multicomponent systems have been developed.

The term "single-component materials" is understood to mean reactive materials which all already comprise the monomeric constituents, the solid powder component and the initiators which are necessary to initiate the polymerization of these reactive monomers. Unlike the powder/liquid system, the material is ready for use without one or more components having to be added through further admixing. The difficulty consists in stabilizing the monomers from premature polymerization so that the material remains stable on storage for a relatively long period of time (approximately 6 months at 28° C.).

The conventional single-component systems include heat-polymerizable materials based on vinyl chloride/vinyl acetate (VC/VAc) copolymers known under the names Luxene® and Luxident®. Benzoyl peroxide is used as catalyst. The disadvantages of the materials concerned are the high price, the complicated process, the poor stability on storage and the tendency towards discoloration during or after polymerization.

The powder/liquid systems comprising methyl methacrylate (MMA) known from the state of the art have disadvantages because MMA is volatile and leaves behind, without special packing measures, after relatively long handling in air or in nonairtight receptacles, a dried-out material which can be processed with difficulty and, because of the uncontrolled loss of MMA, exhibits variable properties after polymerization.

For this reason, single-component materials without methyl methacrylate have been developed. Such materials are described, for example, in U.S. Pat. No. 5,502,087, EP 0 630 641 A1 and EP 0 687 451 A2. For example, single-component materials based on di- or polyfunctional (meth)acrylates are prepared which comprise crosslinked polymers based on polymethyl methacrylate (PMMA) and/or inorganic fillers. Inhibited initiators, such as long-chain peresters or initiators copolymerized in crosslinked PMMA beads, protect from premature polymerization. Such systems are therefore not stable on storage because the bead polymer present therein turns into a dough during storage and thus results in stiffening in consistency. Apart from this, the known heat-curing materials exhibit even further disadvantages: they are very brittle, can be polished with difficulty and are not clinically stable.

Furthermore, however, materials based on MMA/PMMA (Injectall®, Fricke) are also known. Such heat-curing single-component materials are composed of an impact-resistant modified suspension polymer which has been swollen in MMA. The dough achieves, after dissolution of the polymer, a viscosity which remains constant for a relatively long period of time during storage. However, such a mixture is not suitable for general filling technology since, for satisfactory processability, the content of polymer may only be 40-50%. Because of the limited stability on storage, the material is prepared and dispatched to order.

Light-curing single-component materials are also known from the state of the art. Such light-curing composite materials do not comprise any MMA and are, like their heat-curing counterparts, likewise protected from drying. The disadvantages are high brittleness, poor ability to be polished, inhibition of the basal surface and poor chemical stability.

Light-curing materials are discriminating as the light source of the known systems does not reach and accordingly cure all places uniformly. In addition, the adhesion of the teeth to such materials is unsatisfactory.

Self-curing paste systems are furthermore known (e.g., Ivopast® IVAG). These paste systems are composed of at least two pastes in which the initiators (e.g., peroxides) and the accelerators (e.g., amines) are included separately. Such paste systems are well known as filling materials, composite-based crown and bridge materials and dual-curing restoration composites and cements. Two-paste systems for the preparation of prostheses are, on the other hand, unknown.

According to the abovementioned state of the art, such pastes, which are processed as dental prosthetics materials, are to be stabilized and inhibited so that a stability on storage for at least one year at a mean temperature of 23±5° C. is guaranteed. The danger arises, through inhibition, be it through addition of inhibiting substances, such as stabilizers, or through use of inhibiting peroxides, which only form radicals at relatively high temperature, of excessively poor polymerization and whitish mottling as a result of a high content of residual monomer. In order for the quality of these prosthetic materials to be acceptable, relatively long processing times have to accepted, in order for the material to satisfactorily cure, or the stability on storage is guaranteed by a systematic cooling of the product up to use.

Another problem is the handling of such paste systems. In order to keep the viscosity constant over the period of time mentioned, the PMMA (co)polymers have to be completely dissolved, or insoluble solid particles are dispersed in a relatively high content of monomer. As a result of this, such a system shrinks more than is the case with known powder/liquid mixtures of two-component prosthetic materials. Such a paste system is then dependent on a special heat-curing application process, such as, e.g., an injection system, or light curing.

The use of industrial polysulfones in thermoplastic prosthetic materials is known from DE-OS 36 08 409. These thermoplastics are processed analogously to injection molding, which results in high costs for the technology necessary. Unlike the known powder/liquid systems, these materials exhibit serious disadvantages. The noncrosslinked thermoplastic, when the prosthetic is in place in the mouth, is susceptible to corrosion due to stress-cracking and has unsatisfactory adhesion to the embedded teeth. In addition, the plastic may separate poorly from the plaster since, under high injection pressure and at the high processing temperature, the plaster decomposes locally and the hardened alginate release agents are no longer effective.

EP 0 760 249 B1 describes a process for the production of connected microgel particles and articles treated with connected microgel particles. A homogeneous composite results from the formation of interpenetrating polymer networks. The preparation of dental prostheses is not revealed in this document.

WO 2004/113042 A2 teaches a composition which can be used for rapid prototyping. The materials are characterized in that solid polymer particles are wetted at the surface with a monomer with adhesive properties and are subsequently polymerized. The monomers are dissolved before penetration. For example, polysulfones or polyethersulfones can be dissolved in bisphenol A diglycidyl ether.

U.S. Pat. No. 2,793,436 describes the preparation of false teeth or tooth parts. In this connection, inorganic fibers are incorporated as reinforcing agents in a monomer mixture and processed to give a paste.

EP 059 525 B1 describes dental mixtures in which use is made, in addition to soluble polymers, of even larger amounts of an insoluble (swellable) crosslinked polymer. The completely swollen crosslinked polymer is, in a second stage, mixed with addition of acrylic acid and silica gel to give a ready-to-use paste. Use of polysulfones is not known from this state of the art.

Polysulfones have already been used for decades in medical technology, the optical industry and electrical engineering. For example, U.S. Pat. No. 6,605,651 B1 proposes the use of polysulfones as thermoplastic polymer constituent in polymerizable dental mats. Polysulfone is admittedly mentioned as one of several thermoplastic components which can be used.

Further embodiments for the processing of polysulfones are not available. FDA authorizations have been given for a broad range of polysulfone types just for use in medical technology.

It is now the object of the present invention in particular to correct the disadvantages known from the state of the art of single-component systems. The materials obtained should in particular be characterized by improved handling properties. In addition, flexural strength, fracture toughness, transparency and the chemical stability should be optimized. However, the objective of the present invention is not limited to single-component systems. Rather systems should also be made available in which, e.g., initiators are stored separately and are introduced in the case of the processing.

This object is achieved by moldable materials comprising a mixture of:
  from 20 to 50% by weight of at least one polymerizable monomer suitable for dental purposes and
  from 50 to 80% by weight of at least one polysulfone-based polymer suitable for dental purposes which is at least partially swollen in at least a portion of the monomer,
the amounts adding up to 100% by weight each time.

A subject matter of the invention is furthermore a process for the preparation of moldable materials, in which
  from 20 to 50% by weight of at least one polymerizable monomer suitable for dental purposes and
  from 50 to 80% by weight of at least one polysulfone-based polymer suitable for dental purposes are mixed, and
  the polymer is at least partially swollen in at least a portion of the monomer,
the amounts adding up to 100% by weight each time.

A subject matter of the present invention is likewise the use of the moldable materials according to the invention and also of the products prepared according to the process according to the invention in the preparation of dental products, preferably in the preparation of dental prostheses.

The moldable materials are available in particular in the form of flowable systems. Liquids, dispersions, suspensions, melts, solid mixtures or thermoplastic systems are preferably concerned. Particular preference is given to the use of the moldable materials according to the invention in the form of pastes.

Preferred compositions of the moldable materials according to the invention comprise between 55 and 75% by weight of polymer and between 25 and 45% by weight of monomer.

The preferred reactive monomers include methyl methacrylate, ethyl methacrylate, butyl methacrylate, ethyl acrylate, butyl acrylate, hydroxyethyl (meth)acrylate monomethyl ether, neopentyl glycol propoxyloxy methyl ether mono(meth)acrylate, ethylene glycol dimethacrylate, butanediol dimethacrylate, ethoxylated bisphenol A dimethacrylate (SR 348C) and ethoxylated cyclohexanedimethanol dimethacrylate.

Unlike polycarbonate, polyether (ether) ketone, polyetherimide or polyether (ether) sulfone, polysulfones are satisfactorily swellable or even soluble in mono(meth)acrylates and short-chain polar di(meth)acrylates. The polysulfone granule or powder can swell and dissolve in the monomers through a swelling or dissolution process accelerated at 60° C. in the heat. The components are dispersed in suitable mixers, such as, e.g., a Z-arm kneader. The shear forces occurring in this connection and the frictional heat arising from the kinetic energy give rise to a uniform distribution of the polymer phase in the monomer.

Conventional polysulfones industrially with low molar masses from approximately 20 kDa to approximately 32 kDa are suitable as polymer component in the above-mentioned monomers for the preparation of prosthetic materials and are equivalent or even superior in the mechanical properties to the MMA/PMMA materials prepared in the powder/liquid process. The flexural strength and the fracture toughness may in this connection be brought out as particular characteristics but even the transparency and the stability with regard to hot aqueous dye solutions and dietary components are at least equivalent to those of PMMA/(meth)acrylate compositions. The low molar masses of the polysulfones and the polymerizable materials prepared therefrom guarantee good handling properties for the dental technician, even at a polymer content of up to 75% by weight.

The polymerizable materials described can be used for different systems.

Possible embodiments are single- and two-paste systems. In addition to a single-paste material, which consists only of one component and can be cured with heat, two-paste systems are also possible.

The single-paste systems comprise only one initiator which can be activated by introduction of energy. Peroxides, such as dibenzoyl peroxide, dilauroyl peroxide, tert-butyl peroctoate, tert-butyl perbenzoate or di(tert-butyl) peroxide, are preferably suitable as initiators. Typical compositions comprise inhibited peroxides, peroxyesters, perketals or nitriles (dibenzoyl peroxide, dilauroyl peroxide, di(tert-butylperoxy)(trimethyl)cyclohexane, tert-butyl peroxyethylhexanoate or 1,1'-azobis(cyclohexanecarbonitrile)).

In contrast to the above, the two-paste systems comprise the components of the initiator system divided up between the two pastes: one paste is provided with the redox accelerator (activator) necessary for the splitting (e.g., tertiary amines, such as N,N-dimethyl-p-toluidine, N,N-dihydroxyethyl-p-toluidine, ethyl p-(dimethylamino)benzoate or structurally related systems, such as xylidines or anilines (N,N'-dimethyl-sym-xylidine, N,N'-di(2-hydroxyethyl)-sym-xylidine or N,N-diethyl-sym-di(tert-butyl)aniline), while the other paste comprises the splittable initiator, e.g., a diacyl peroxide (e.g., dibenzoyl peroxide, dimethoxydibenzoyl peroxide, dilauroyl peroxide, didodecanoyl peroxide or dilauryl peroxydicarbonate).

It is likewise possible to conceive of the use of light-curing systems. This system is composed of a material which can be polymerized with light and which comprises photoinitiators, e.g. phosphine oxides, triphenylphosphine oxides or thioxanthones. Photo-initiators (cf J. P. Fouassier and J. F. Rabek (editors), Radiation Curing in Polymer Science and Technology, Vol. II, Elsevier Applied Science, London and New York, 1993) for the UV or visible region, such as benzoin ethers, dialkylbenzil ketals, dialkoxyacetophenones, acyl- or bisacylphosphine oxides, α-diketones, such as 9,10-phenanthrenequinone, diacetyl, furil, anisil, 4,4'-dichlorobenzil, 4,4'-dialkoxybenzil and camphorquinone, are suitable in particular. Furthermore, use may also be made of azo compounds, such as 2,2'-azobis-(isobutyronitrile) (AIBN) or azobis(4-cyanovaleric acid).

The invention is more fully described below with the help of examples.

EXAMPLE 1

Transparent Heat-Cured Resin for Orthodontic Plates or Transparent Palatal Plates 1. Preparation of a Preswollen Material
   0.65 kg of Ultrason S 3010 (melt flow index MFI=8 g/10 min, 343° C., 2.16 kg, according to ISO 1133) in granular form is introduced into a receptacle and treated with 0.35 kg of benzyl methacrylate. The granules are then preswollen at 60° C. in a preheating oven for at least 20 hours. The swollen material is homogenized using a Z-arm kneader insofar as a nonsticky and transparent material devoid of nodules and streaks is present.
2. Preparation of the Polymerizable Material
   0.5 kg of the preswollen homogeneous material is introduced into a Z-arm kneader and kneaded with 20 g of benzyl methacrylate until a homogeneous dough is obtained. In order to render the material polymerizable, 6 g of lauroyl peroxide are incorporated in the material present.
3. Filling
   The material is squeezed into a film bubble closed on one side. After filling, the bag is closed by welding or using metal clips.
4. Use
   An orthodontic palatal plate made of wax is invested in a metal flask from Universal-Presstechnik (Kaneda, K. "Grundkonzept für ästhetische Vollprothese" [Fundamental concept for aesthetic full prosthesis], Quintessenz Zahntechnik 16/7 (1990)). After hardening of the plaster, the plaster plate is boiled out with hot water. After thoroughly cooling the plaster, the plaster mold is isolated with conventional alginate release agent.
   The film bubble is opened and the amount of the material necessary, inclusive of an excess, is removed from the packaging. The dough is then placed in the isolated plaster die of the flask, provided with the counterpart half and pressed in a hydraulic press. The excess squeezed out in this connection is discarded. The flask from the pressing is fixed using a flask clamp and then introduced into a heatable water bath with cold water at 23° C. The water bath is then heated up to 100° C. After reaching the boiling point of the water, the flask is cooked for 45 min. The flask is then removed from the bath and cooled down to ambient temperature over 30 minutes. After an additional cooling time of half an hour under cold flowing water, the orthodontic plate is removed from the mold.

EXAMPLE 2

Pink-Colored Heat-Cured Resin for the Injection Technique

1. Preparation of Color Concentrates
   Dispersing of Pigments Using a Pulverulent Polysulfone:
   14.85 kg of Udel P 1800 NT (MFI=6-7 g/10 min, 343° C., 2.16 kg, according to ISO 1133) are introduced into a Dierks mixer.
   0.015 kg of an iron oxide pigment, of an azo pigment or of a titanium dioxide pigment are dispersed in the polysulfone in the Dierks mixer in 3 minutes at 1000 revolutions/minute with water cooling.

2. Preparation of a Preswollen Material 0.65 kg of Ultrason S 3010 (MFI=8 g/10 min, 343° C., 2.16 kg) in granular form is introduced into a receptacle and treated with 0.35 kg of benzyl methacrylate. The granules are then preswollen at 60° C. in a preheating oven for at least 20 hours. The swollen material is homogenized using a Z-arm kneader insofar as a nonsticky and transparent material devoid of nodules and streaks is present.

3. Preparation of the Polymerizable Material 366 g of the preswollen homogeneous material are introduced into a Z-arm kneader and treated with 6.6 g of benzyl methacrylate until a homogeneous dough is obtained. 3.3 g of the color concentrate mixture from 1 are then added to the kneader batch and kneading is carried out for long enough for the dough to acquire a uniform color and to be devoid of streaks and nodules.

In order to render the material polymerizable, 0.75 g of lauroyl peroxide is kneaded into the material present until a homogeneous paste with a uniform pink-whitish coloring is obtained.

4. Filling

The material is squeezed into a film bubble closed on one side. After filling, the bag is closed by welding or using metal clips.

5. Use

Before creating the wax prosthesis, the necks of the teeth sticking into the plaster counter are roughened and provided with retention recesses. As additional improvement to the adhesion of the teeth, the necks of the teeth are extensively coated with pure methyl methacrylate.

A wax prosthesis is invested on the model side in the flask half of an Ivocap® injection flask (DE 23 12 934). The plaster counter is then prepared. As soon as the plaster has hardened, the wax plate is boiled out with hot water. After the plaster has been thoroughly cooled, all the plaster surfaces are isolated with conventional alginate release agent.

The film bubble is opened and the amount of the material necessary, inclusive of an excess, is removed from the packaging, filled into an empty Ivocap cartridge case and provided with the plunger belonging to it.

According to Kaneda, K., "Grundkonzept für ästhetische Vollprothese" [Fundamental concept for aesthetic full prosthesis], Quintessenz Zahntechnik 16/7 (1990), the Ivocap flask is clamped in a clamping frame provided for the Ivocap system and cartridge case with plunger and funnel are then introduced into the centering insert belonging to the flask.

The pressure attachment is put on and the material is then injected into the inside of the flask for 5 minutes. The flask is heated in boiling water for 35 minutes. The hot flask is then, along with the clamping frame, cooled down under cold flowing water for 30 minutes.

At the end of this time, the prosthesis is removed from the mold, completed and polished.

EXAMPLE 3

Self-Curing Two-Paste Material

1. Preparation of Color Concentrates

The color concentrates are prepared analogously to the exemplary embodiment described above.

2. Preparation of a Preswollen Material 0.28 kg of Ultrason S 6010 (MFI=5 g/10 min, 343° C., 2.16 kg) or Udel P 3500 NT (MFI=3-5 g/10 min, 343° C., 2.16 kg) is introduced into a receptacle and treated with 0.17 kg of methyl methacrylate. The granules are then preswollen at 60° C. in an oven for at least 20 hours. After 20 hours, the surviving methyl methacrylate is poured off and discarded. The swollen material is now homogenized using a Z-arm kneader for long enough for a nonsticky and transparent paste devoid of nodules and streaks to be present.

3. Preparation of the Initiator Paste 80 g of the preswollen homogeneous material are introduced into a Z-arm kneader and diluted with 14 g of methyl methacrylate until a homogeneous dough is obtained. 6.7 g of the color concentrate mixture from 1 are then added to the material and kneaded for long enough for the dough to achieve a uniform color and to be devoid of streaks and nodules. 16 g of SR-348 C are then kneaded portionwise into the dough until a malleable and homogeneous paste again results. In order to render the material polymerizable, 2 g of lauroyl peroxide are kneaded into the material present until a homogeneous uniform whitish-colored paste is obtained.

4. Preparation of the Accelerator Paste 80 g of the preswollen homogeneous material are introduced into a Z-arm kneader and diluted with 14 g of methyl methacrylate until a homogeneous dough is obtained. 6.7 g of the concentrated mixture from 1 are then added to the material and kneading is carried out for long enough for the dough to achieve a uniform color and to be finally devoid of streaks and nodules. 16 g of SR-348 C are then kneaded portionwise into the dough until a malleable and homogeneous paste again results. In order to render the material polymerizable, 1 g of N,N-diethanol-p-toluidine is kneaded into the material present until the crystals are completely dissolved and a uniformly colored paste is obtained.

5. Filling

Initiator paste and accelerator paste are squeezed separately into film bubbles closed on one side. These are filled quickly. After filling, the bags are again closed.

6. Use

Before creating the wax prosthesis, the necks of the teeth are roughened and provided with retention recesses. As additional improvement to the adhesion of the teeth, the necks of the teeth are extensively coated with pure methyl methacrylate.

A wax prosthesis is invested in the flask half of a metal flask. After the plaster has hardened, the plaster plate is boiled out with boiling hot water. After the plaster has thoroughly cooled, the plaster mold is isolated with conventional alginate release agent.

The film bags are opened and the necessary amounts of each paste are removed in equal portions from the packagings. The two pastes are then mixed by hand for approximately 60 seconds. The mixed dough is placed in the isolated plaster die of the flask, provided with the counter half and pressed under the hydraulic press.

The excess squeezed out in this connection is discarded. The pressed flask is placed in an autoclave under 2.2 bar with water of 50° C. and subsequently polymerized for 20 min. The flask is then removed from the autoclave and cooled down under flowing water for 5 minutes. The ready-for-use prosthesis is, as usual, removed from the mold, completed and polished.

EXAMPLE 4

Light-Curing Prosthetic Material

1. Preparation of Color Concentrates

The color concentrates are prepared analogously to the exemplary embodiment described above.

2. Preparation of a Preswollen Material
   0.25 kg of Udel P 1800 NT is introduced into a receptacle and treated with 0.25 kg of phenoxyethyl methacrylate. The granules are then preswollen at 60° C. in a preheating oven for at least 20 hours. The swollen material is homogenized using a Z-arm kneader for long enough for a nonsticky and transparent material devoid of nodules and streaks to be present.
3. Preparation of the Polymerizable Material
   500 g of the preswollen homogeneous material are introduced while protected from the light into a Z-arm kneader and treated with 5 g of Lucirin® TPO until the photoinitiator is dissolved and a homogeneous dough is obtained.
4. Filling
   The pasty dough is deaerated under vacuum in the kneader while protected from the light and stored in black cans. The paste can also be extruded in films in order to obtain prefabricated plates or sausage-shaped rims which are used for the preparation of base plates for the relining or as basis for the tooth set-up.
5. Use
   A plaster model with base cast is created. This is isolated with alginate solution. A prefabricated plate is now placed on the dried alginate film and adjusted by hand to the plaster model. The molded plate is then illuminated, together with the plaster model, for 15 minutes in a Spectramat® or in a Lumamat® (power: max. 750 watts, 400-580 nm, fluorescent tubes, both Ivoclar Vivadent AG, Schaan). After illuminating, the cured plate is taken away from the plaster model and then illuminated for a further 15 minutes with the side, earlier facing the plaster, now being directed upwards opposite the light source.
   After illumination, the teeth can be directly waxed-up on this plate. The base plate then acts as individual impression tray which is not discarded but is used as base plate for the prosthesis. This is the advantage in comparison with conventional impression tray materials, which cannot be used for the physiological application and, after the mark-up, lose their function for the finished product.

Formulation 1: Heat-Curing Single-Component Prosthetic Material

| Components | Content |
| --- | --- |
| Polysulfone (MFI = 3-18 g/10 min, 343° C., 2.16 kg) Udel (Solvay ® Corporation) or Ultrason S (BASF AG) | 38.5-69.35% |
| Monomethacrylate | 30-45% |
| Pigments | 0.1-0.3% |
| Diacyl peroxide, perester | 0.5-1% |
| Ethoxylated bisphenol A dimethacrylate (SR348 C) | 0-15% |
| tert-Butyl-ortho-cresol | 0.05-0.2% |

Formulation 2: 2-Component Paste Self-Curing Resin
Composition of the Accelerator Paste

| Components | Content |
| --- | --- |
| Polysulfone (MFI = 3-18 g/10 min, 343° C., 2.16 kg) Udel (Solvay ® Corporation) or Ultrason S (BASF AG) | 37.5-69.35% |
| Monomethacrylate | 30-45% |
| Pigments | 0.1-0.3% |
| Tertiary amine | 0.5-2% |
| SR348 C | 0-15% |
| HALS stabilizer | 0.05-0.2% |

Composition of the Initiator Paste

| Components | Content |
| --- | --- |
| Polysulfone (MFI = 3-18 g/10 min, 343° C., 2.16 kg) Udel (Solvay ® Corporation) or Ultrason S (BASF AG) | 37.8-69.45% |
| Monomethacrylate | 30-45% |
| Pigments | 0.1-0.3% |
| Diacyl peroxide | 0.5-2% |
| SR348 C | 0-15% |
| tert-Butyl-ortho-cresol | 0.05-0.2% |

Formulation 3: Light-Curing Single-Component Prosthetic Material

| Components | Content |
| --- | --- |
| Polysulfone (MFI = 3-18 g/10 min, 343° C., 2.16 kg) Udel (Solvay ® Corporation) or Ultrason S (BASF AG) | 37.8-69.45% |
| Monomethacrylate | 30-45% |
| Pigments | 0.1-0.3% |
| Triphenylphosphine oxide or camphorquinone | 0.5-2% |
| SR348 C | 0-15% |

Physical Properties

Flexural strength and flexural modulus according to ISO 1567:1999 Examples 2-4

| Variants | Flexural strength [MPa] | E modulus [MPa] |
| --- | --- | --- |
| Example 2: Colored heat-curing single-component material, e.g. for the injection technique | 98 ± 1 | 3055 ± 40 |
| Example 3: Self-curing two-paste material | 85 ± 5 | 2710 ± 95 |
| Example 4: Light-curing prosthetic material | 86 ± 0.5 | 2750 ± 55 |

Fracture toughness according to ISO 20795—Part 1 (Working Draft 2005)

| Variants | Fracture work [J/m$^2$] | $K_{max}$ value [MPa · m$^{1/2}$] |
| --- | --- | --- |
| Example 2: Colored heat-curing single-component material, e.g. for the injection technique | 840 ± 225 | 2.2 ± 0.1 |
| Example 3: Self-curing two-paste material | 1225 ± 195 | 2.9 ± 0.1 |
| Example 4: Light-curing prosthetic material | 250 ± 45 | 1.6 ± 0.1 |

Comparison with the state of the art
Flexural strength and flexural modulus according to ISO 20795-1

| Variants | Flexural strength [MPa] | E modulus [MPa] |
|---|---|---|
| Heat-curing single-component material, Puran ® HC (Novodent, Schaan) | 63.5 ± 6.5 | 2000 ± 50 |
| Heat-curing single-component material for the injection technique, Injectall HI-I/C-F (Fricke Corp.) | 78 ± 1.5 | 2280 ± 45 |
| Self-curing resin based on PMMA, ProBase Cold (Ivoclar Vivadent AG) | 68 | 2550 |
| Light-curing prosthetic material, Versyo.com (Heraeus Kulzer GmbH) | 108.5 ± 5.5 | 2810 ± 75 |

Fracture toughness according to ISO 20795—Part 1

| Variants | Fracture work [J/m$^2$] | $K_{max}$ value [MPa·m$^{1/2}$] |
|---|---|---|
| Heat-curing single-component material, Puran ® HC (Novodent, Schaan) | 82 ± 3 | 0.68 ± 0.04 |
| Heat-curing single-component material for the injection technique, Injectall HI-I/C-F (Fricke Corp.) | 940 ± 90 | 1.95 ± 0.1 |
| Self-curing resin based on PMMA, ProBase Cold (Ivoclar Vivadent) | 400 ± 100 | 1.5 ± 0.1 |
| Light-curing prosthetic material, Versyo.com (Heraeus Kulzer GmbH) | 60 ± 10 | 0.77 ± 0.14 |

The invention claimed is:

1. A moldable dental material comprising a mixture of:
   from 20 to 50% by weight of at least one polymerizable monomer suitable for dental purposes and
   from 50 to 80% by weight of at least one polysulfone-based polymer suitable for dental purposes which is at least partially swollen in at least a portion of the monomer,
   the amounts adding up to 100% by weight each time.

2. The moldable material as claimed in claim 1, wherein it comprises from 25 to 45% by weight of monomer and from 55 to 75% by weight of polymer, the amounts adding up to 100% by weight each time.

3. The moldable material as claimed in claim 1, wherein it comprises (meth)acrylates as polymerizable monomers.

4. The moldable material as claimed in claim 1, wherein it comprises, as polymerizable monomers, mono(meth)-acrylates or short-chain di(meth)acrylates or mixtures thereof.

5. The moldable material as claimed in claim 1, wherein it comprises initiators.

6. The moldable material as claimed in claim 1, wherein it comprises initiators which can be activated by introduction of energy.

7. The moldable material as claimed in claim 6, wherein it comprises peroxides as initiators.

8. The moldable material as claimed in claim 1, wherein it comprises activators.

9. The moldable material as claimed in claim 8, wherein it comprises, as activators, amines or mixtures thereof.

10. The moldable material as claimed in claim 1, wherein it comprises photoinitiators.

11. The moldable material as claimed in claim 10, wherein it comprises, as photoinitiators, camphorquinone, azo compounds, phosphine oxides or thioxanthones.

12. The moldable material as claimed in claim 1, wherein the initiators and/or activators are stabilized or inhibited.

13. A process for the preparation of the moldable material as claimed in claim 1, wherein
   from 20 to 50% by weight of at least one polymerizable monomer suitable for dental purposes and
   from 50 to 80% by weight of at least one polysulfone-based polymer suitable for dental purposes are thus mixed with one another, and
   the polysulfone is at least partially swollen in at least a portion of the monomer,
   the amounts adding up to 100% by weight each time.

14. The process as claimed in claim 13, wherein from 25 to 45% by weight of monomer and from 55 to 75% by weight of polymer are used, the amounts adding up to 100% by weight each time.

15. A process of using the moldable dental material claimed in claim 1 comprising fabricating a dental product with the moldable dental material.

16. The process of claim 15, wherein the dental product comprises a dental prosthesis.

* * * * *

UNITED STATES PATENT AND TRADEMARK OFFICE
CERTIFICATE OF CORRECTION

PATENT NO. : 8,436,070 B2
APPLICATION NO. : 12/310185
DATED : May 7, 2013
INVENTOR(S) : Rheinberger et al.

Page 1 of 1

It is certified that error appears in the above-identified patent and that said Letters Patent is hereby corrected as shown below:

Title page, item (22) should read:

--(22) PCT Filed: Aug 8, 2007--

Title page, item (86) should read:

--(86) PCT No.: PCT/EP2007/058230
§ 371 (c)(1),
(2), (4) Date: Jul. 6, 2010--

Title page, item (87) should read:

--(87) PCT Pub. No.: WO2008/019978
PCT Pub. Date: Feb. 21, 2008--

Signed and Sealed this
Fifteenth Day of October, 2013

Teresa Stanek Rea
*Deputy Director of the United States Patent and Trademark Office*

UNITED STATES PATENT AND TRADEMARK OFFICE
CERTIFICATE OF CORRECTION

PATENT NO. : 8,436,070 B2  Page 1 of 1
APPLICATION NO. : 12/310185
DATED : May 7, 2013
INVENTOR(S) : Rheinberger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1098 days.

Signed and Sealed this
Eighth Day of September, 2015

Michelle K. Lee
*Director of the United States Patent and Trademark Office*